United States Patent [19]
Wall, Jr.

[11] Patent Number: 6,114,370
[45] Date of Patent: Sep. 5, 2000

[54] AMNESIC SEDATION COMPOSITION AND METHOD OF ADMINISTERING SAME

[76] Inventor: William H. Wall, Jr., 5139 Jimmy Carter Blvd., Norcross, Ga. 30093

[21] Appl. No.: 09/406,355

[22] Filed: Sep. 28, 1999

Related U.S. Application Data

[60] Provisional application No. 60/102,036, Sep. 28, 1998.
[51] Int. Cl.⁷ .......................... A61K 31/40; A61K 31/55; A61K 31/44
[52] U.S. Cl. ........................ 514/410; 514/220; 514/294
[58] Field of Search .................................. 514/410, 220, 514/294

[56] References Cited

U.S. PATENT DOCUMENTS

| | | | |
|---|---|---|---|
| 4,873,076 | 10/1989 | Fishman et al. | 424/10 |
| 5,234,929 | 8/1993 | Chelen | 514/269 |
| 5,756,745 | 5/1998 | Kavka | 546/44 |

*Primary Examiner*—Theodore J. Criares
*Assistant Examiner*—Jennifer Kim
*Attorney, Agent, or Firm*—Needle & Rosenburg, P.C.

[57] ABSTRACT

This invention relates to a pharmaceutical amnesic sedation composition for administering to a subject comprising an effective of: (i) a benzodiazepine derivative, (ii) a phenanthrene derivative, and (iii) an anticholinergic agent. This invention also relates to a method of administering to a subject a pharmaceutical amnesic sedation composition comprising: (a) preparing a pharmaceutical amnesic sedation composition of this invention, and (b) administering to a subject a therapeutically effective amount of the composition that sedates the subject.

11 Claims, No Drawings

AMNESIC SEDATION COMPOSITION AND METHOD OF ADMINISTERING SAME

CROSS REFERENCE TO RELATED APPLICATION

This application claims the benefit of provisional patent application Ser. No. 60/102,036, filed Sep. 28, 1998, which is incorporated herein by this reference in its entirety.

BACKGROUND OF THE INVENTION

1. Field of the Invention

This invention relates generally to an amnesic sedation pharmaceutical composition having few or no side effects and a method of administering the composition to a subject.

2. General Background

Medications used as sedatives, anesthetics, analgesics and/or amnesics are known. For example, midazolam hydrochloride, a water-soluble benzodiazepine derivative, is an agent for use in conscious sedation of surgical patients and, in some cases, for providing amnesia of the period of the agent's administration. The effect this agent has on the receiving patient includes loss or impairment of recall of any procedure performed during the course of the drug's administration. However, the loss or impairment of recall is not known to affect long term memory.

Adverse reactions to sedatives including midazolam hydrochloride include, but are not limited to, respiratory depression, apnea, respiratory arrest and/or cardiac arrest, sometimes resulting in death. There have also been rare reports of hypotensive episodes requiring treatment during or after diagnostic or surgical manipulations in patients who have received midazolam hydrochloride, for example. Other adverse reactions include nausea, coughing, headache, drowsiness, tenderness, redness, phlebitis and associated allergic reactions.

Nalbuphine hydrochloride is a synthetic narcotic agonist-antagonist analgesic of the phenanthrene series. Adverse reactions to nalbuphine hydrochloride include sweatiness, nausea, dizziness, dry mouth, and headaches. Other adverse reactions that may occur include central nervous system effects, such as nervousness, depression and restlessness and cardiovascular effects such as hypertension and hypotension.

Scopolamine hydrobromide is a pharmacological belladonna alkaloid with anticholinergic properties. It has proven to be a clinically effective agent for the prevention of nausea and vomiting associated with motion sickness in adults, for example. The most frequent adverse reaction to scopolamine hydrobromide is dryness of the mouth. A less frequent adverse reaction is drowsiness. Transient impairment of eye combination, including blurred vision and dilation of the pupils, is also observed.

The infrequent adverse reactions of scopolamine hydrobromide include, but are not limited to, disorientation, memory disturbances, dizziness, restlessness, hallucinations, confusion, and the like. Withdrawal symptoms include dizziness, nausea, headache and disturbances of equilibrium.

The foregoing agents or the families of these agents, taken singularly, all have adverse effects. Therefore, the need exists for an amnesic sedation agent with similar pharmacological properties to these agents, yet has limited or reduced adverse effects.

Accordingly, the present invention provides for an amnesic sedation composition having the beneficial aspects of the foregoing individual agents while limiting their adverse effects.

SUMMARY OF THE INVENTION

In accordance with the purpose(s) of this invention, as embodied and broadly described herein, this invention, in one embodiment, relates to a pharmaceutical amnesic sedation composition for administering to a subject comprising an effective amount of: (i) a benzodiazepine derivative, (ii) a phenanthrene derivative, and (iii) an anticholinergic agent.

In another embodiment, this invention relates to a method of administering to a subject a pharmaceutical amnesic sedation composition comprising: (a) preparing a pharmaceutical amnesic sedation composition of this invention, and (b) administering to a subject a therapeutically effective amount of the composition that sedates the subject.

In yet another embodiment, this invention relates to a pharmaceutical composition for administering to a subject comprising an effective amount of: (i) at least one sedative to sedate a subject, (ii) at least one analgesic to relieve pain in the subject and (iii) a anticholinergic agent.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention. Before the present composition, formulations and method are disclosed and described, it is to be understood that this invention is not limited to specific methods or to particular formulations, as such may, of course, vary. It is also to be understood that the terminology used herein is for the purpose of describing particular embodiments only and is not intended to be limiting.

It must also be noted that, as used in the specification and the appended claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

In one embodiment, the amnesic sedation composition of this invention generally comprises (i) a benzodiazepine derivative, (ii) a phenanthrene derivative, and (iii) an anticholinergic agent. These derivatives and agents are known in the art and any of such derivatives and/or agents are useful for use in the composition of the present invention.

Preferably, the amnesic sedation composition of this invention comprises midazolam hydrochloride (a benzodiazepine derivative), nalbuphine hydrochloride (a phenanthrene derivative) and scopolamine hydrobromide (an anticholinergic agent).

Midazolam hydrochloride is a well known agent for use in sedation. Chemically, midazolam hydrochloride is 8-chloro-6-(2-fluorophenyl)-1-methyl-4H-imidazo[1,5-a][1,4] benzodiazepine hydrochloride. Midazolam hydrochloride is a short acting water-soluble benzodiazepine central nervous system depressant. The effects of this agent on the central nervous system are dependent on the dose administered, the route of administration, and the presence or absence of other premedications. Additionally, when midazolam hydrochloride is given intravenously as an anesthetic induction agent, sedation occurs within a time period dependent upon the total dose administered and the concurrent administration of narcotic premedications.

Midazolam hydrochloride may be administered to a patient and introduced into the body by injection, for example. It is typically injected intramuscularly for preoperative sedation (induction of sleepiness or drowsiness and relief of apprehension) and to impair memory of perioperative events. Further, it may be injected intravenously as an agent for conscious sedation prior to short diagnostic or endoscopic procedures, such as bronchoscopy, gastroscopy, cystoscopy, coronary angiography and cardiac catheterization, either alone or with a narcotic. Midazolam hydrochloride may also be injected intravenously for induction of general anesthesia, before administration of other anesthetic agents.

Nalbuphine hydrochloride is a synthetic narcotic agonist-antagonist analgesic of the phenanthrene series. Chemically, nalbuphine hydrochloride is (−)-17-(cyclobutylmethyl)-4,5α epoxymorphinan-3,6α1-4-triol hydrochloride. This agent is a potent analgesic. Its analgesic potency is essentially equivalent to that of morphine. That is, the agent may be used or is indicated for the relief of moderate to severe pain. It can also be used as a supplement to balanced anesthesia or preoperative and postoperative analgesia.

Scopolamine hydrobromide is a pharmacological anticholinergic belladonna alkaloid with well known properties. It has proven to be a clinically effective agent for the prevention of nausea and vomiting associated with motion sickness in adults. The drug has a long history of oral and parenteral use for central anticholinergic activity. The mechanism of action of scopolamine hydrobromide in the central nervous system is not definitely known but induces anticholinergic effects. "Anticholinergic agent," as used herein to describe the present invention, means any agent that attenuates the function of a cholinergic receptor.

Preferably, the amnesic sedation composition of this invention is in a homogenous solution, and more preferably a homogenous aqueous solution. The composition comprises components in a general ratio of approximately 1 (benzodiazepine derivative):1(phenanthrene derivative):0.1 (anticholinergic agent). Further, a 40% variation of the ratio of the amounts of the foregoing benzodiazepine and phenanthrene derivative components and a 10% variation of the anticholinergic agent may be used, if desired.

The dosage of the composition and the components therein varies depending on the type of effect desired, on the weight, age, sex of the subject, and the method of administration. Generally, compositions can be orally or intravenously administered in an amount based on an average weight of a subject (about 60 kg). Necessary modifications in the dosage range may be determined by one of ordinary skill in the art using only routine experimentation given the teachings known in the art. The dosage can also be adjusted by the individual physician in the event of any complication.

Preferably, a homogenous solution of the composition of the present invention comprises from about 3 to about 7 mg of midazolam hydrochloride, from about 3 to about 7 mg of nalbuphine hydrochloride, and from about 0.35 to about 0.55 mg of scopolamine hydrobromide. More preferably, the composition of this invention comprises a dosage of approximately 5 mg of midazolam hydrochloride, approximately 5 mg of nalbuphine hydrochloride and approximately 0.43 mg of scopolamine hydrobromide.

It is apparent to a person skilled in the art that other embodiments of the present invention may be made by varying the ratio of the composition components to one another. In addition, the dosages and/or concentrations of each of the components can be varied depending on the effects desired.

The amnesic sedation composition of this invention, preferably a solution, has beneficial effects not found in the component drugs singularly. The solution has good shelf life with the components of the composition being completely miscible. In addition, the incidence of allergy to the solution is very low.

When in solution, the composition is homogenous and is preferably used as a sedation agent that is extremely useful for outpatient surgical procedures. The medication provides not only sedation, but also excellent amnesia. The medication enhances the effects of local anesthesia. The solution also is safe from the depression of normal vital signs such as blood pressure, heart rate, respiration and blood oxygenation. There is a reasonably safe and broad dose range before an overdose is experienced.

A surprising and unexpected benefit of the composition of this invention over the known agents taken singularly is the extremely low incidence of adverse side effects such as nausea, vomiting, hypotension, dizziness, tachycardia, bradycardia, palpitations and/or other side effects following the use of the medication. Moreover, the therapeutic effect of the present amnesic sedation medication lasts for 3–5 hours and the patient is usually very quickly ambulatory after a surgical procedure lessening the need for a recovery facility. Recovery for the sedation episode is rapid and without the usual hangover.

In another embodiment, this invention provides for a method of administering the pharmaceutical composition of this invention. The method comprises (a) preparing a pharmaceutical amnesic sedation composition of this invention, and (b) administering to a subject a therapeutically effective amount of the composition that sedates the subject.

When the composition is administered to the subject in a therapeutically effective amount, the effect of the composition on the subject receiving the composition includes loss or impairment of recall of any procedure performed during the course of the drug's administration. However, the loss or impairment of recall is not known to affect long term memory. One skilled in the art would know how to determine the efficacy of the administration of the composition.

In general, "a therapeutically effective amount" is that amount of the composition needed to achieve the desired result or results, e.g., sedation, amnesia, anticholinergic activity, and/or pain relief. The amount necessary to achieve the desired result would preferably be an amount that achieves these desired results, yet reduces or eliminates adverse side effects. One of ordinary skill in the art will recognize that the potency and, therefore, a "therapeutically effective amount" can vary for the various agents used in the composition of this invention. One skilled in the art can readily assess the potency of a candidate composition that provides sedation, amnesia, pain relief and/or anticholinergic effects.

The pharmaceutical amnesic sedation composition of this invention may be administered to a patient in need thereof by commonly employed methods or techniques for administering an agent in such a way to bring the agent in contact with or introduce into the subject's body. In one embodiment, the injection of a solution of the composition is well received subcutaneously, intramuscularly or intravenously and is not a painful irritant to body tissues.

The composition of the present invention may also be administered orally, parenterally, topically, transdermally, extracorporeally, topically or the like, although parenteral administration is typically preferred. Parenteral administration of the agents of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous, intra-articular and intratracheal routes. A more recently revised approach for parenteral administration involves use of a slow release or sustained release system such that a constant dosage is maintained. See, e.g., U.S. Pat. No. 3,610,795, which is incorporated by reference herein in order to more fully describe the state of the art to which this invention pertains. The agents can also be administered using polymer based delivery systems, including, for example, microencapsulation.

The pharmaceutical composition of this invention can be administered conventionally as compositions containing the active components as a predetermined quantity of active material calculated to produce the desired therapeutic effect in association with the required diluent, i.e., carrier or vehicle. Depending on the intended mode of administration, the components can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected components in combination with a pharmaceutically acceptable carrier and, in addition, may include other medicinal agents, pharmaceutical agents, carriers, adjuvants, diluents, etc.

By "pharmaceutically acceptable" is meant a material that is not biologically or otherwise undesirable, i.e., the material may be administered to an individual along with the selected agent without causing any undesirable biological effects or interacting in a deleterious manner with any of the other components of the pharmaceutical composition in which it is contained.

Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Thus, the compositions are administered in a manner compatible with the dosage formulation and in a therapeutically effective amount. As discussed above, precise amounts of the active agents of the mixture required to be administered depend on the judgment of the practitioner and are peculiar to each individual.

Parenteral administration, as preferred in this invention, is generally characterized by injection or intravenous delivery. Injectables can be prepared in conventional forms, either as liquid solutions or suspensions, solid forms suitable for solution or suspension in liquid prior to injection or intravenous delivery, or as emulsions.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pharmaceutical amnesic sedation composition for administering to a subject comprising an effective amount of a homogenous solution of:
   (i) a benzodiazepine derivative comprising midazolam hydrochloride,
   (ii) a phenanthrene derivative comprising nalbuphine hydrochloride, and
   (iii) an anticholinergic agent comprising scopolamine hydrobromide;
wherein the component (i): component (ii): component (iii) ratio is approximately 1:1:0.1.

2. The composition of claim 1, wherein component (i) is midazolam hydrochloride present in an amount of about 3 mg to about 7 mg/administration.

3. The composition of claim 1, wherein component (i) is midazolam hydrochloride present in an amount of about 5 mg/administration.

4. The composition of claim 1, wherein component (ii) is nalbuphine hydrochloride present in an amount of about 3 mg to about 7 mg/administration.

5. The composition of claim 1, wherein component (ii) is nalbuphine hydrochloride present in an amount of about 5 mg/administration.

6. The composition of claim 1, wherein component (iii) is scopolamine hydrobromide present in an amount of about 0.35 mg to about 0.55 mg/administration.

7. The composition of claim 1, wherein component (iii) is scopolamine hydrobromide present in an amount of about 0.43 mg/administration.

8. The composition of claim 1, wherein component (i) is midazolam hydrochloride present in an amount of about 5 mg, component (ii) is nalbuphine hydrochloride present in an amount of about 5 mg, component (iii) is scopolamine hydrobromide present in an amount of about 0.43 mg, and components (i), (ii) and (iii) are in a homogenous solution.

9. A method of administering to a subject a pharmaceutical amnesic sedation composition comprising:

(a) preparing a pharmaceutical amnesic sedation composition of claim 1, and (b) administering to a subject a therapeutically effective amount of the composition that sedates the subject.

10. The method of claim 9, wherein the subject is a human being.

11. The method of claim 9, wherein the composition is parenterally administered to the subject.

* * * * *

UNITED STATES PATENT AND TRADEMARK OFFICE
CERTIFICATE OF CORRECTION

PATENT NO : 6,114,370
DATED : September 5, 2000
INVENTOR(S) : William H. Wall, Jr.

It is certified that error appears in the above-identified patent and that said Letters Patent are hereby corrected as shown below:

Title page, column 2, item [57] Abstract, line 4, after "effective" insert --amount--.

Signed and Sealed this

Fifteenth Day of May, 2001

Attest:

NICHOLAS P. GODICI

*Attesting Officer*      *Acting Director of the United States Patent and Trademark Office*